United States Patent [19]
Ohno et al.

[11] Patent Number: 5,227,299
[45] Date of Patent: Jul. 13, 1993

[54] NADH KINASE AND A PROCESS FOR PRODUCING THE SAME

[75] Inventors: Tsuyoshi Ohno, Matsudo; Masaru Suzuki; Tatsuo Horiuchi, both of Nagareyama, all of Japan

[73] Assignee: Noda Institute for Scientific Research, Japan

[21] Appl. No.: 822,906

[22] Filed: Jan. 21, 1992

[30] Foreign Application Priority Data

Jan. 25, 1991 [JP] Japan ................. 3-007998

[51] Int. Cl.$^5$ .................. C12N 9/12; C12P 21/04
[52] U.S. Cl. .................. 435/194; 435/71.1; 435/938
[58] Field of Search ............ 435/7.91, 183, 194, 435/938, 71.1, 71.2, 193

[56] References Cited

U.S. PATENT DOCUMENTS

| | | | |
|---|---|---|---|
| 4,411,995 | 11/1983 | Whitesides et al. | 435/90 |
| 4,416,983 | 11/1983 | Röder et al. | 435/25 |
| 4,446,231 | 5/1984 | Self | 435/7.91 |
| 4,501,813 | 2/1985 | Lövgren et al. | 435/8 |
| 4,598,042 | 7/1986 | Self | 435/7.91 |
| 4,766,071 | 8/1988 | Simon et al. | 435/90 |
| 4,769,321 | 9/1988 | Self | 435/7.91 |
| 5,032,506 | 7/1991 | Palmer et al. | 435/26 |

FOREIGN PATENT DOCUMENTS 58-129994 3/1983 Japan.
59-213400 3/1984 Japan.

OTHER PUBLICATIONS

Yumiko Iwahashi, et al. Characterization of NADH Kinase from *Saccharomyces cerevisiae*, J. Biochem. 105, 588–593 (1989).

Yumiko Iwahashi, et al. Localization of the NADH Kinase in the Inner Membrane of Yeast Mitochondria, J. Biochem 105, 916–921 (1989).

Yumiko Iwahashi, et al, Orientation and Reactivity of NADH Kinase in Proteoliposomes, J. Biochem., 105, 922–926 (1989).

Seikagaku Zikken Koza, Biochemical Experiments, vol. 5, pp. 121–131.

*Primary Examiner*—Douglas W. Robinson
*Assistant Examiner*—Kristin K. Larson
*Attorney, Agent, or Firm*—Banner, Birch, McKie & Beckett

[57] ABSTRACT

The present invention relates to a novel NADH kinase which has high stability and is specific for NADH, and a process for producing the NADH kinase by culturing a yeast belonging to the genus Pichia in a culture medium, and this enzyme permits highly sensitive determination of NADH alone and hence is useful in the field of clinical medicine.

4 Claims, 5 Drawing Sheets

NADH KINASE AND A PROCESS FOR PRODUCING THE SAME

BACKGROUND OF THE INVENTION

The present invention relates to a novel NADH kinase and a process for producing the same.

DESCRIPTION OF THE PRIOR ART

There is widely employed a diagnostic method in which the amount of a substance capable of serving as a marker of pathosis is determined using an enzymatic reaction. However, there exist trace markers which are difficult to measure by conventional methods and the amount of a test fluid is limited to a slight amount in some cases, for example, medical examinations of newborn babies. Highly sensitive analytical methods capable of solving such problems are being required in the art.

One such method is a sensitizing analytical method using a cycling reaction. As the cycling reaction, there are known $\beta$-NAD$^+\rightleftarrows\beta$-NADH cycling reaction, $\beta$-NADP$^+\rightleftarrows\beta$-NADPH cycling reaction, etc. ["Seikagaku Jikken Koza (Biochemical Experiments)", Vol. 5, p. 121–131]. For example, as disclosed in Japanese Patent Unexamined Publication No. 59-213400, $\beta$-NAD$^+$ may be determined with high sensitivity by phosphorylating only $\beta$-NAD$^+$ in a solution containing $\beta$-NADH and $\beta$-NAD$^+$, into $\beta$-NADP$^+$ by the use of a kinase specific for $\beta$-NAD$^+$, and subjecting the $\beta$-NADP$^+$ to the cycling reaction.

However, when a slight amount of NADH is present in a mixture comprising NAD$^+$ and NADH, it cannot be determined by the above method disclosed in Japanese Patent Unexamined Publication No. 59-213400. Therefore, there has heretofore been employed a flow injection assay using HPLC and a method comprising boiling (Japanese Patent Unexamined Publication No. 58-129994), but these methods are disadvantageous in that they require an expensive apparatus, a troublesome procedure and a long period of time. There is also a highly sensitive method comprising allowing $\beta$-NADH to cause luminescence by the use of luciferase and a method comprising allowing $\beta$-NADH to cause chemiluminescence, but these methods require a special and expensive detector and involve the problem of the stability of reagents.

If there is a kinase which is stable and highly specific for NADH, the above determination of NADH becomes possible. However, no NADH kinase of practical use is known. Although several NADH kinases have been reported, some of them do not have marked specificity, some others have no specificity, and some others have specificity but are very unstable. Therefore, they cannot be put to practical use in combination with various enzymatic reactions for carrying out highly sensitive measurement.

SUMMARY OF THE INVENTION

In consideration of such conditions, the present inventors earnestly investigated obtaining a stable NADH kinase which is suitable for practical use and specific for NADH. Consequently, it was found that a yeast belonging to the genus Pichia may produce the desired NADH kinase, whereby the present invention was accomplished.

An object of the present invention is to provide a novel NADH kinase having the following physicochemical properties (hereinafter referred to as "the present enzyme").

(1) Action

The present enzyme, as shown in the reaction formula given below, catalyzes a reaction by which from substrates NADH and XTP [wherein X is A (adenosine), U (uridine), G (guanosine), C (cytidine), I (inosine), dT (thymidine), dA (deoxyadenosine), dU (deoxyuridine), dG (deoxyguanosine), dC (deoxycytidine), or dI (deoxyinosine)], NADPH and XDP (wherein X is as defined above) are produced through phosphorylation of NADH in the presence of at least one kind of ion selected from the group consisting of Mg$^{2+}$, Mn$^{2+}$, Ca$^{2+}$ and Co$^{2+}$ ions.

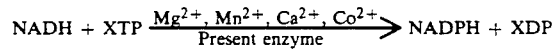

$$\text{NADH} + \text{XTP} \xrightarrow[\text{Present enzyme}]{\text{Mg}^{2+},\ \text{Mn}^{2+},\ \text{Ca}^{2+},\ \text{Co}^{2+}} \text{NADPH} + \text{XDP}$$

wherein X is as defined above.

(2) Substrate specificity

The present enzyme is very specific for NADH and hardly acts on NAD$^+$.

The substrate specificity of the present enzyme was examined under the following reaction conditions.

TABLE 1

| Substrate solution | |
|---|---|
| 10 mM NADH or NAD$^+$ | 0.2 ml |
| 0.5 mM HEPPS* buffer (pH 8.5) | 0.1 ml |
| 10 mM ATP | 0.3 ml |
| 0.1M magnesium chloride | 0.1 ml |
| 2.0M sodium acetate | 0.1 ml |
| Distilled water | 0.1 ml |
| | 0.9 ml |

*HEPPS: N-2-Hydroxyethylpiperazine-N'-3-propanesulfonic acid

To 0.9 ml of each of the above substrate solutions containing NADH or NAD$^+$ was added 0.1 ml of 23 U/ml of the present enzyme, and the reaction was carried out at 30° C. for 20 minutes. Then, the reaction was terminated by heat treatment at 100° C. for 2 minutes, and the denatured protein was removed, after which the amount of NADPH or NADP$^+$ produced by the reaction of the corresponding substrate was measured as follows. As a control solution, there was used a mixture of each substrate solution and the present enzyme in which the reaction had been terminated immediately after mixing them.

With 1 ml of each of the reaction solutions obtained in the above was mixed 1 ml of a color-producing solution consisting of 10 mM G-6-P, 50 mM HEPPS buffer (pH 8.0), 10 mM magnesium chloride, 0.1% bovine serum albumin, 2.5 IU/ml G-6-P dehydrogenase (NADP$^+$-dependent), 5 IU/ml diaphorase and 250 $\mu$M 2,6-dichlorophenolindophenol. The resulting mixture was immediately introduced into a constant-temperature cuvette of STASAR III spectrophotometer of Gilford and subjected to reaction at 30° C. Simultaneously with the reaction, the change of absorbance at 600 nm was measured with the lapse of time, and the difference ($\Delta$OD$_{600\ nm}$/min) between absorbance values 1 minute and 2 minutes after the initiation of the coloration reaction was taken as a measured value. As to relative activity (%), a measured value ($\Delta$OD$_{600\ nm}$/min) obtained by using NAD$^+$ as a substrate was shown as a percentage based on a measured value ($\Delta OD_{600\ nm}$/min) obtained by using NADH as a substrate.

The results obtained are as follows:

| Substrate | Relative activity (%) |
|---|---|
| NADH | 100 |
| NAD⁻ | 0.9 |

(3) Measuring method of titer

TABLE 2

| Substrate solution | |
|---|---|
| 10 mM NADH | 0.2 ml |
| 0.5M HEPPS buffer (pH 8.5) | 0.1 ml |
| 10 mM ATP | 0.3 ml |
| 0.1M magnesium chloride | 0.1 ml |
| 2.0M sodium acetate | 0.1 ml |
| Distilled water | 0.1 ml |
| | 0.9 ml |

0.9 Milliliters of the above substrate solution containing NADH was preheated to 30° C., after which 0.1 ml of a solution of the present enzyme was added, and the reaction was carried out at 30° C. for 20 minutes. Thereafter, the reaction was terminated by heat treatment at 100° C. for 2 minutes, and the denatured protein was removed. Then, the amount of NADPH produced by the reaction of the substrate was measured as follows. As a control solution, there was used a mixture of the substrate solution and the present enzyme in which the reaction had been terminated immediately after mixing them.

With 1 ml of each of the reaction solutions obtained above was mixed 1 ml of a color-producing solution having the same composition as that of the color-producing solution described in the above item "Substrate specificity". The resulting mixture was immediately introduced into a constant-temperature cuvette of STASAR III spectrophotometer of Gilford and subjected to reaction at 30° C. Simultaneously with the reaction, the change of absorbance at 600 nm was measured with the lapse of time, and the difference ($\Delta OD_{600\ nm}$/min) between absorbance values 1 minute and 2 minutes after the initiation of the coloration reaction was obtained as a measured value. By the use of a calibration curve of $\Delta OD_{600\ nm}$/min versus NADPH concentration previously prepared using NADPH solutions of known concentrations, the amount of the NADPH produced was calculated from the measured value.

An amount of the enzyme at which NADPH is produced in an amount of 1 nano-mole per minute at 30° C., is taken as 1 unit.

The Km value (Michaelis constant) of the present enzyme for NADH is 27 micromoles at 30° C. and pH 7.8 (Tris buffer).

(4) Optimum pH

The optimum pH of the present enzyme is, as shown in FIG. 1, pH 8.0-9.0 when NADH is used as a substrate.

(5) pH range for stability

The present enzyme was dissolved in each of buffer solutions of various pH, and after standing at 4° C. for 16 hours, the residual activity was measured to find that the enzyme was stable at pH 7.0-9.0 as shown in FIG. 2.

(6) Range of temperature suitable for action

The range of temperature suitable for action of the present enzyme is 30° to 45° C. as shown in FIG. 3.

(7) Thermal stability

The present enzyme was dissolved in a buffer solution, and after standing at each temperature for 10 minutes, the residual enzymatic activity was measured, whereby the thermal stability was measured. Consequently, the present enzyme showed residual activity percentages of 83% at 35° C., 60% at 40° C., and 30% at 45° C. as shown in FIG. 4.

(8) Inhibition, activation and stabilization

The present enzyme is strongly inhibited by SDS (sodium lauryl sulfate), p-CMB (p-chloromercuribenzoic acid), $Pb^{2+}$, $Zn^{2+}$, $Cd^{2+}$, $Cu^{2+}$, $Hg^{2+}$, etc., and is activated by sodium acetate, etc. In addition, it is stabilized by saccharose, $Mg^{2+}$, $Mn^{2+}$, DTT (dithiothreitol), ammonium sulfate, etc.

(9) Purification method

The present enzyme may be purified by employing conventional methods for purification of enzymes, such as ion-exchange chromatography, ammonium sulfate fractionation, hydrophobic chromatography, gel filtration, etc. singly or in combination of two or more thereof.

(10) Molecular weight

The molecular weight of the present enzyme is about 160,000 daltons as measured by gel filtration using Superose 6 HR10/30 column [mfd. by Pharmacia AB (Sweden)] according to the method of Andrews [Biochem. J. 96, 595 (1965)].

(11) Isoelectric point

The isoelectric point of present enzyme is pI=6.40 as measured by electrophoresis by the use of an agarose gel containing an ampholyte.

Comparison between the present enzyme and NADH kinases described in well-known references, i.e., NADH kinase A (J. Biochem. 105, 588–593, 1989) and NADH kinase B (J. Biochem. 247, 1473–1478, 1972), is as shown in Table 3.

TABLE 3

| | Present enzyme | A | B |
|---|---|---|---|
| Source | pichia membranaefaciens | Saccharomyces cerevisiae | Saccharomyces cereviciae |
| Optimum pH | 8.5 | 8.5 | 8.0–8.5 |
| Thermal stability | 10% inactivated at 35° C. in 5 min. 17% inactivated at 35° C. in 10 min. | 65% inactivated at 35° C. in 5 min. | Very unstable |
| Specificity | NADH = 100 NAD⁺ = 0.9 | NADH = 100 NAD⁺ = 1.7 | NADH = 100 NAD⁺ = 1.6 |
| Molecular weight | 160,000 | 160,000 | |

As is clear from Table 3, the present enzyme is different from the known NADH kinases in enzymological and physicochemical properties and is superior to them particularly in thermal stability. Therefore, the present enzyme may be advantageously applied for practical use such as highly sensitive analysis and may be used in combination with other various enzymes.

DESCRIPTION OF THE PREFERRED EMBODIMENTS

Figure 1:
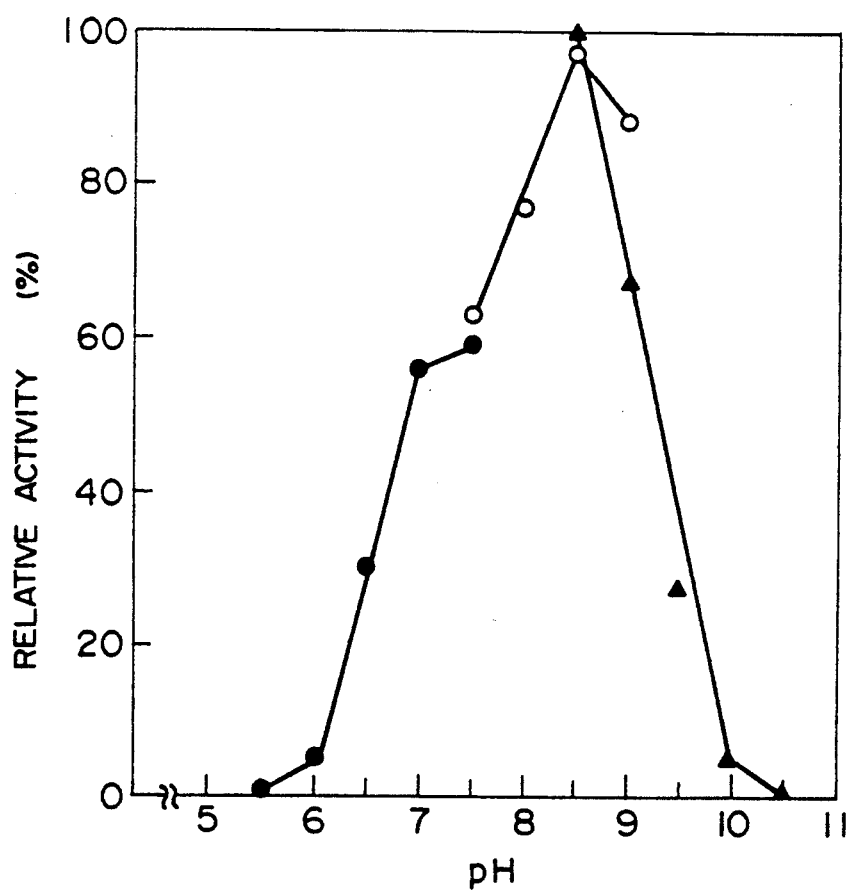
FIG. 1 is a graph showing the optimum pH of the present enzyme (●-●: phosphate buffer, O-O: Tris-HCl buffer, ▲-▲: glycine-sodium hydroxide buffer).
Figure 2:
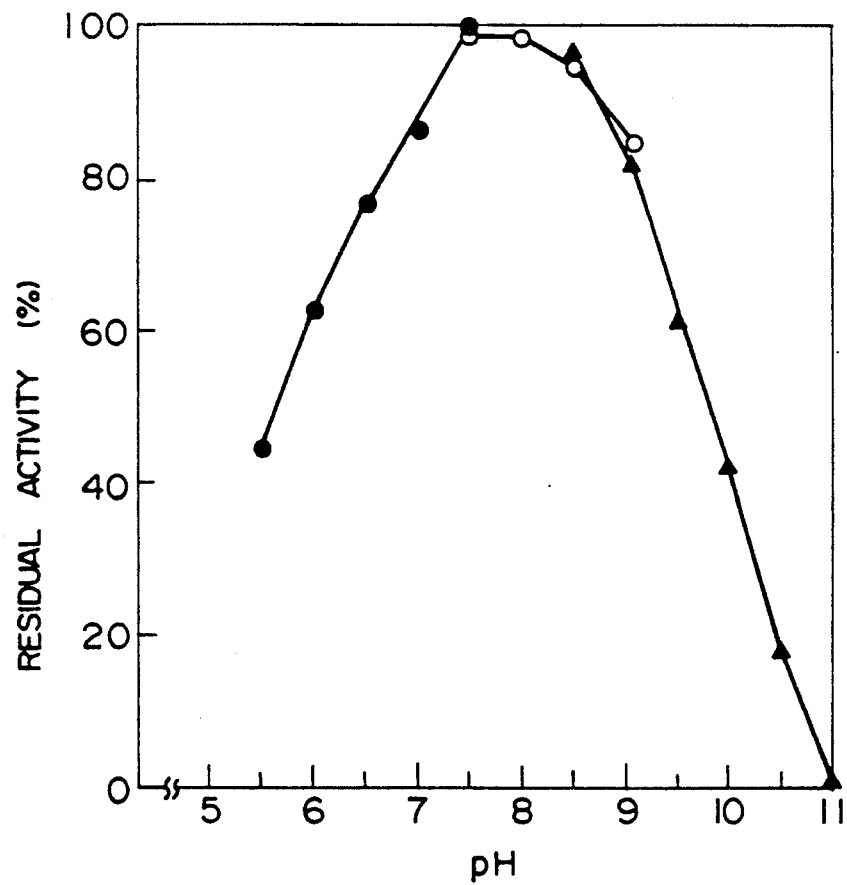
FIG. 2 is a graph showing a pH range for stability of the present enzyme (●-●: : phosphate buffer, O-O: Tris-HCl buffer, ▲-▲: glycine-sodium hydroxide buffer).
Figure 3:
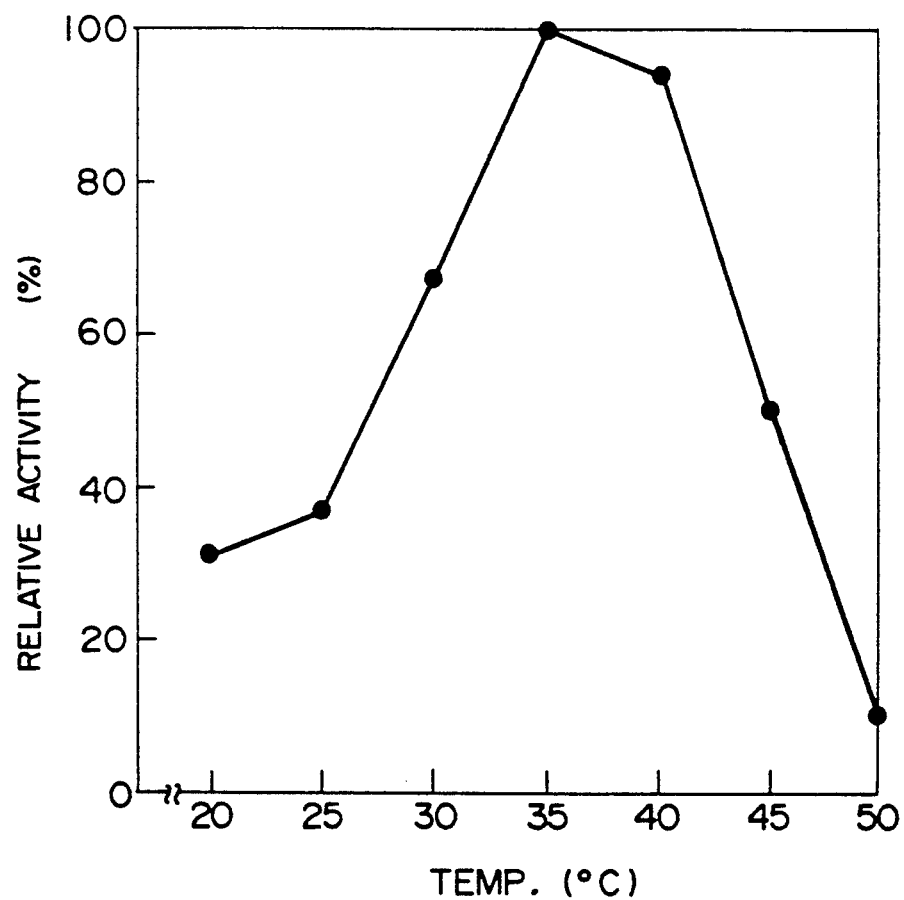
FIG. 3 is a graph showing a range of temperature suitable for action of the present enzyme.
Figure 4:
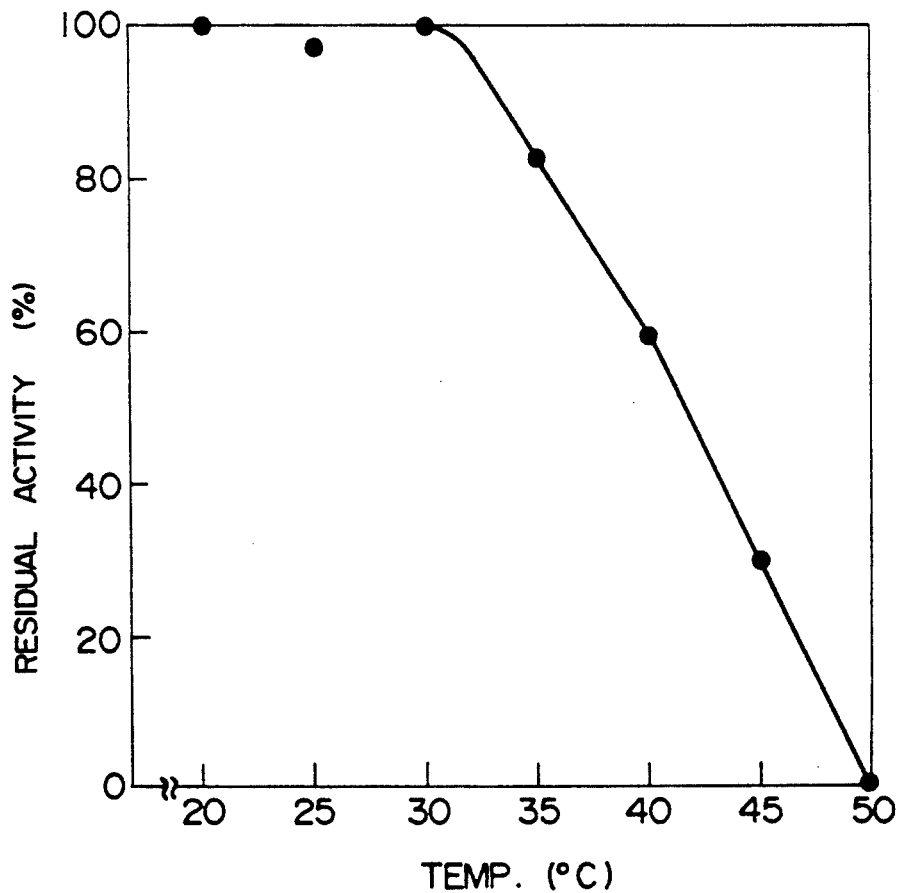
FIG. 4 is a graph showing the thermal stability of the present enzyme.

A process for producing the present enzyme is described below.

As yeast used in the present invention, any strain may be used so long as it belongs to the genus Pichia and has NADH-kinase-producing ability. A specific example of the yeast is *Pichia membranaefaciens* YS27 strain. Varieties and variants of this strain may also be used.

*Pichia membranaefaciens* YS27 strain is a strain newly separated from soil in Utsunomiya City, Tochigi Prefecture, Japan by the present inventors, and its mycological properties are as follows.

When the strain is cultured in YM agar medium at 25° C. for 5 days, its colonies have a dimly lustrous yellowish-tan.

By observation under an optical microscope, ovoidal vegetative cells are observed, and the strain proliferates by multipolar budding. When colonies formed by cultivation of the strain in modified Gorodkowa agar medium at 25° C. for 5 days are observed under an optical microscope, spheroidal or ellipsoidal asci containing four ascospores are usually observed. The ascospores are circular and tend to be released from the asci. No true hypha is observed, but pseudohyphae grow well. The strain forms climbing pellicles on the surface of culture broth and is aerobic. The strain does not produce a carotenoid type dye.

The strain cannot utilize nitrates, cannot ferment glucose, and has no strong formation of acid. Additionally, this strain cannot utilize maltose, galactose, trehalose, mannitol, salicin and potassium gluconate.

The strain was identified as *Pichia membranaefaciens* on the basis of the above mycological properties by reference to "The Yeasts, A Taxonomic Study the third edition".

The strain was named *Pichia membranaefaciens* YS27 and deposited as Bikoken Joki No. 3,208 (FERM BP-3208) under Budapest Treaty in Fermentation Research Institute, Agency of Industrial Science and Technology (Bikoken), Ministry of International Trade and Industry.

As a culture medium used in the present invention, there may be used either synthetic media or natural media, which contain carbon sources, nitrogen sources, inorganic substances, and other nutrients. As the carbon sources, there may be suitably used, for example, glucose, citric acid, and glycerin. As the nitrogen sources, there may be suitably used, for example, peptone, yeast extract, malt extract, meat extract and ammonium sulfate. As the inorganic substances, there may, if necessary, be used salts of sodium, manganese, magnesium, calcium, etc., phosphates, and the like. As to cultivation conditions, shaking culture or cultivation with stirring and aeration is carried out usually at 20°-40° C., preferably about 30° C., for 4 to 48 hours. The pH at the initiation of cultivation is usually 5.0-7.5, preferably about 6.0.

The present enzyme may be accumulated in cells in a larger amount by adding a substance present in or near the citric acid cycle, for example, succinic acid, lactic acid or citric acid. These substances may be added to the medium either at the first stage or at an optional stage of cultivation course.

The cultivation may be terminated at a time at which the titer of the present enzyme reaches a maximum during the cultivation.

Since the present enzyme exists usually intracellularly, the cells are collected from a culture mixture by filtration, centrifugation or the like and disintegrated, for example, by a mechanical disintegrating means such as glass beads treatment or French press treatment, or an enzymatic disintegrating means using a lytic enzyme for yeast, or the like. In this case, if necessary, the enzyme may be liberated into a solution by solubilizing the same by addition of a solubilizing agent such as Triton X-100. The thus obtained solution containing the enzyme is freed of nucleic acids and cell walls by a conventional method, and the insoluble materials are removed from the residue by filtration, centrifugation or the like, whereby the present enzyme may be obtained.

The present enzyme may be purified by employing conventional methods for purification of enzymes, such as ion-exchange chromatography, ammonium sulfate fractionation, hydrophobic chromatography or gel filtration singly or in proper combination of two or more thereof.

Experimental Example

Determination of NADH by the use of the NADH kinase of the present invention

Figure 5:
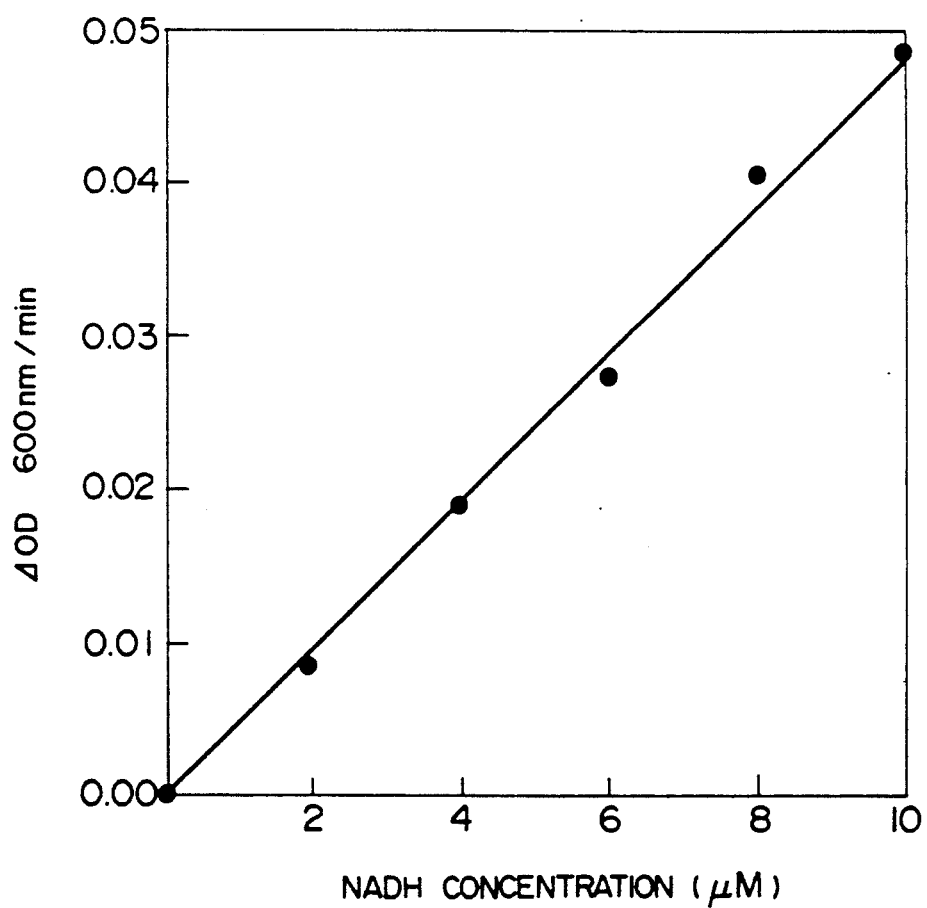
FIG. 5 is a calibration curve obtained in Experimental Example by plotting $\Delta OD_{600\,nm}$/min against NADH concentration.

For determining a slight amount of NADH present in a system containing a large amount of NAD+, 0.4 ml of a sample solution containing 2 mM NAD+ and each concentration (0 to 10 μM) of NADH was added to 0.8 ml of a reagent solution having the composition of reagent solution I shown below, and the reaction was carried out at 35° C. for 20 minutes. After terminating the reaction, 0.8 ml of a reagent solution having the composition of reagent solution II shown below was mixed with the reaction solution, and the resulting mixture was immediately introduced into a constant-temperature cuvette of STASAR III spectrophotometer of Gilford and subjected to reaction at 30° C. Simultaneously with this reaction, the change of absorbance at 600 nm was measured with the lapse of time, whereby the difference ($\Delta OD_{600\,nm}$/min) between absorbance values 1 minute and 2 minutes after the initiation of the coloration reaction was obtained as a measured value. Consequently, as shown in FIG. 5, good linearity could be attained between NADH concentration and $\Delta OD_{600\,nm}$/min with high sensitivity. Composition of reagent solution I:

Composition of reagent solution I:

| | -continued |
|---|---|
| 100 mM | HEPPS buffer (pH 8.5) |
| 7.5 mM | ATP |
| 15 mM | magnesium chloride |
| 0.3 M | sodium acetate |
| 10 U/ml | NADH kinase |
| | Composition of reagent solution II: |
| 10 mM | G-6-P |
| 50 mM | HEPPS buffer (pH 8.0) |
| 10 mM | magnesium chloride |
| 0.1% | bovine serum albumin |
| 2.5 IU/ml | G-6-P dehydrogenase (NADP+-dependent) |
| 5 IU/ml | diaphorase |
| 300 μM | 2,6-dichlorophenolindophenol |

The present invention provides a novel NADH kinase which has a high stability and is specific for NADH. It further provides a process for producing the NADH kinase by culturing a yeast belonging to the genus Pichia. When the present enzyme is used, a slight amount of NADH alone may be determined with high sensitivity even in a mixture comprising NAD+ and NADH. Therefore, the NADH kinase is industrially very useful in the fields of clinical medicine, etc.

The present invention is illustrated below in detail with reference to Example.

Example: Preparation of NADH kinase

Pichia membranaefaciens YS27 (FERM BP-3208) was inoculated into 50 ml of culture medium A (pH 5.5) consisting of 2% glucose, 1% yeast extract, 1% peptone, 0.9% monopotassium hydrogenphosphate, 0.6% ammonium sulfate, 0.05% calcium chloride and 0.05% magnesium sulfate in a 500-ml Sakaguchi flask, and was subjected to shaking culture at 30° C. for 24 hours. The seed culture thus obtained was inoculated into 20 liters of culture medium A and cultured at 30° C. for 18 hours in a 30-liter jar fermentor under conditions of an aeration rate of 20 liters/min and an agitation rate of 300 r.p.m. The resulting culture was collected by centrifugation to obtain 1,406 g of cells. The whole cells were inoculated into 20 liters of culture medium B (pH 5.5) consisting of 0.5% glucose, 1% yeast extract, 1% peptone, 0.9% monopotassium hydrogenphosphate, 0.6% ammonium sulfate, 0.05% calcium chloride, 0.05% magnesium sulfate and 2% sodium succinate, and cultured at 30° C. for 6 hours in a 30-liter jar fermentor under conditions of an aeration rate of 20 liters/min and an agitation rate of 300 r.p.m. The resulting culture was collected by centrifugation to obtain 1,428 g of cells. The whole cells were dispersed in 50 mM phosphate buffer (pH 6.0) containing 0.1 M saccharose and 0.5% Triton X-100, to make a total volume of 5 liters. The resulting dispersion was ground by the use of glass beads with a DYNO-MILL [WAB (Switzerland)].

Then, 5,280 ml of the liquid ground product recovered was freed of precipitate by centrifugation, after which the buffer (pH 6.0) containing 0.05 M sodium chloride by using an ultrafiltration membrane (cut-off molecular weight: 6,000 daltons).

Subsequently, 5,260 ml of the enzyme solution thus obtained was passed through a CM-Sephadex C-50 column (Pharmacia AB) previously buffered with 10 mM phosphate buffer (pH 6.0) containing 0.05 M sodium chloride, to be adsorbed thereon, and was washed with 10 mM phosphate buffer (pH 6.0) containing 0.1 M sodium chloride. Thereafter, elution was carried out by means of a sodium chloride concentration gradient of 0.1 to 0.4 M to collect an active fraction.

The buffer in 455 ml of the eluate was replaced by 10 mM HEPPS buffer (pH 7.5) containing 10% ammonium sulfate and 5 mM $MgCl_2$ by using an ultrafiltration membrane (cut-off molecular weight: 6,000 daltons). The solution thus obtained was passed through a Phenyl-Toyopearl 650 column (Tosoh Ltd.) previously buffered with the same buffer as above, to be adsorbed thereon, and was washed with 10 mM HEPPS buffer (pH 7.5) containing 10% ammonium sulfate and 5 mM $MgCl_2$. Then, elution was carried out be means of an ammonium sulfate concentration gradient of 10 to 0% to collect an active fraction.

Subsequently, 372 ml of the eluate was concentrated to a volume of 25 ml by the use of an ultrafiltration apparatus (cut-off molecular weight: 10,000 daltons) mfd. by Amicon, and charged into a Sephacryl S-300 HR column (mfd. by Pharmacia AB) previously buffered with 10 mM HEPPS buffer (pH 7.5) containing 0.2 M ammonium sulfate and 5 mM $MgCl_2$, and gel filtration was carried out. The active fraction thus obtained was concentrated and then freeze-dried to obtain 117.3 mg (recovery: 34%) of a preparation of the present enzyme. The specific activity of this preparation was 102 U/mg.

What is claimed is:

1. An NADH kinase comprising the following physicochemical properties:

(a) Action and substrate specifity:

the NADH kinase catalyzes a reaction by which NADH and XDP are produced through phosphorylation, in the presence of at lest one ion selected from $Mg^{2+}$, $Mn^{2+}$, $Ca^{2+}$ and $Co^{2+}$ ions, from substrates NADH and XTP, wherein X is selected from adenosine, uridine, guanosine, cytidine, inosine, thymidine, deoxyadenosine, deoxyuridine, deoxyguanosine, deoxycytidine, and deoxyinosine, and wherein the NADH kinase is specific for NADH with the activity of the NADH kinase for NAD+ being less than 1% of the activity towards NADH, (b) Optimum pH and pH range of stability:

the NADH kinase has an optimum pH of 8.0 to 9.0 when NADH is used as a substrate, while the pH range for stability is 7.0 to 9.0, (c) the NADH kinase has an optimum temperature range for activity of 30° C.–45° C., (d) thermal stability:

the NADH kinase exhibits a residual activity percentage of 83% after heat treatment at 35° C. for 10 minutes, 60% after heat treatment at 40° C. for 10 minutes, and 30% after heat treatment at 45° C. for 10 minutes, and (e) the NADH kinase has molecular weight of about 160,000.

2. A process for producing the NADH kinase of claim 1 comprising culturing a yeast belonging to the genus Pichia and having NADH-kinase-producing ability, in a culture medium, and collecting the NADH kinase from the culture.

3. A process according to claim 2 wherein the microorganism belonging to the genus Pichia is Pichia membranaefaciens YS27 (FERM BP-3208).

4. A process according to claim 2 wherein said culture is a shaking culture or an aerating culture and is carried out at a temperature of 20°–40° C. for 4–48 hours.

* * * * *